United States Patent [19]
Godbille et al.

[11] 3,966,609
[45] June 29, 1976

[54] CHROMATOGRAPHIC DEVICE

[75] Inventors: Etienne Godbille, Villemomble; Lucette Tondu, Bobigny, both of France

[73] Assignee: Roussel-UCLAF, Paris, France

[22] Filed: Feb. 25, 1974

[21] Appl. No.: 445,342

[30] Foreign Application Priority Data
Mar. 1, 1973 France .......................... 73.07278

[52] U.S. Cl. .......................... 210/198 C; 55/386
[51] Int. Cl.² .......................... B01D 15/08
[58] Field of Search .......................... 210/31 C, 198 C; 55/386

[56] References Cited
UNITED STATES PATENTS

| | | | |
|---|---|---|---|
| 3,440,864 | 4/1969 | Blume | 210/198 C X |
| 3,474,908 | 10/1969 | Catravas | 210/198 C |
| 3,483,986 | 12/1969 | Wright | 210/198 C |
| 3,487,938 | 1/1970 | Patterson | 210/198 C |
| 3,511,377 | 5/1970 | Hrdina | 210/198 C |
| 3,615,235 | 10/1971 | Hrdina | 210/198 C X |

*Primary Examiner*—John Adee
*Attorney, Agent, or Firm*—Bacon & Thomas

[57] ABSTRACT

A chromatographic device in the form of a tube, adapted to contain a bed of particulate adsorbent material, the tube being provided with a removable, gas and liquid permeable, lid at one end and at the other end with a sliding element permeable to liquids and gas and movable within the tube, the sliding element being provided with means to exert a permanent pressure on the bed of particulate adsorbent material so as to maintain it in the form of a solid body during use and to extrude it from the tube when the lid is removed. The device is used to prepare a bed of particulate adsorbent material, to maintain said bed under pressure during use to avoid movement of particles and to extrude the bed after use.

9 Claims, 4 Drawing Figures

CHROMATOGRAPHIC DEVICE

This invention relates to a chromatographic device. More particularly, it relates to a device for improved preparative chromatography, allowing the chromatographer increased selectivity and efficacity in the treatment of solutions.

There are already numerous chromatographic devices in existence. But where the question of increasing the diameter of columns of preparative chromatography is concerned, the problem of homogeneity of the bed of particulate adsorbent material is soon encountered. In effect, the irregular homogeneity of this bed leads to an irregular hydrodynamic profile and consequently to the establishment of preferential hydrodynamic routes which rapidly diminishes the efficacity and selectivity of the device.

Generally, in traditional chromatography, the particulate adsorbent material is introduced into a column in suspension form in the elution solvent and the compression which is brought about by sedimentation determines a granulometric classification by simple gravity which leads to a longitudinal gradient of the diameter of the adsorbent particles.

The result is poor homogeneity of the bed compression, representing one of the causes of a weak resolution power. This fact constitutes an important flaw in the columns of usual chromatography.

Moreover, proper preparation of classic chromatography, with the aid of the usual columns, necessitates long and delicate work in placement of the particulate adsorbent material.

The possibility of remedying this inconvenience has just now been found as a result of the new apparatus of this invention.

This device can be used to advantage for preparative chromatography on the usual adsorbent material. It can be used, for example, for adsorption chromatography, liquid-liquid chromatography or ion exchangeable resin chromatography.

This apparatus, which permits the realization of wide diameter columns, can also be seen as an appreciable tool in preparative chromatography on a semi-industrial or industrial scale where the quantities of products to fraction are considerable.

The chromatographic apparatus, object of this invention, is preferably in a column form intended to contain a bed of adsorbent material, and made up of a tube comprising on the one hand, at one of the extremities, a lid permeable to liquids and gases and communicating with the exterior and, on the other hand, a sliding element movable the length of the axis of said tube, permeable to liquids and gas and communicating with the exterior, characterized in that the lid situated at one of the extremities is removable and that the sliding element is given a means cooperating with it to communicate the necessary force in order that, while being displaced, it exerts permanently on the bed of adsorbent material contained in the tube a pressure sufficient to confer by compression on this bed, the consistency of a solid body and to extrude this if necessary from the tube once the removable lid is lifted from the tube.

This apparatus is further characterized by the following features:

the removable lid assuring permeability to liquids and gas comprises a porous plate at its base;

the cooperating means for communicating to the sliding element the force necessary to its displacement to the interior of said tube is a pneumatic or hydraulic jack;

the sliding element is in the form of a piston comprising at its head a porous plate assuring its permeability to liquids and gas;

the removable lid communicates with the exterior by the intermediary of a distribution chamber housed at the base of said lid and linked by means of passageways to a distribution cell communicating to the exterior;

the sliding element is in the form of a piston which communicates with the exterior by means of an evacuation cavity housed under the porous plate in the head of said piston and linked to an evacuation passageway leading to the outlet of the apparatus;

the distribution chamber is provided with radically placed bars of a height equal to the depth of the chamber and is linked to the distribution cell by a central passageway and radially placed passageways converging on said cell;

the evacuation cavity is in the form of a sink with radially positioned bars of a height corresponding to the profile of the sink and converging on the central evacuation passageway.

The invention also includes a method of using the apparatus for obtaining an improved bed of adsorbent material for use in chromatography. This method is characterized in that a suspension of particles of adsorbent material is introduced into the tube removed of its lid, the sliding element being at the retracted position of its course, the lid is fitted to the tube, the sliding element is advanced to exert a pressure on said suspension to thereby discharge the liquid through the porous plates and compress the particles between the sliding element and the lid. The sliding element may be used to provide a permanent compression on the adsorbent bed during use so that it has the consistency of a solid body and, if desired, once the chromatographic operations are finished, the lid is removed and the sliding element is advanced to extrude said bed from the tube.

The invention also includes a homogeneous adsorbant bed characterized by the fact that it is obtained by means of the invention's apparatus and method described above.

Another feature of the invention, is the use of a bed of particulate adsorbent material in consolidated state by mechanical pressure in a chromatographic installation in place of the usual chromatographic column.

The apparatus of the invention, while not limited thereto, may comprise the following features:

The porous plate of the lid and of the sliding element are of identical or different qualities. To their advantage, they can be made of stainless sintered steel. The degree of sintering can be controlled to provide the desired porosity of the plate, characterized by the dimensions of its pores. These are, for example, between 6 and 15 $\mu$ but the exact size depends on the nature of the particulate adsorbent material and the granulometry, on the nature of the eluants, and the nature of the materials to be fractioned, as well as on the pressure to which the plates are to be submitted during the operation of the apparatus. The depth of the evacuation cavity and that of the distribution chamber are chosen in terms of the diameters of the columns and consequently the quantities of liquids to be evacuated or distributed; they can vary from 1 to 10 mm. or more according to the diameter of the column. The radially placed bars in the evacuation cavity and in the distribution chamber are intended to facilitate the flow or distribution of liquids and to serve as a support to the respective porous plate during compression of the suspension and compression of the adsorbant bed. According to the preferred method of execution, their lengths is equal to about two-thirds of the diameter of the evacuation cavity or the distribution cavity. Their width is from 2 to 10 mm or more depending on the nature of the tube; of course the number of bars can be increased according to the diameter of the column. The tightness of the sliding element is assured by means of a lip joint of polytetrafluoroethylene of the like. The lid is fixed in any convenient manner, such as by screws, to a tight flange to which is connected the upper end of the tube and the tightness of said lid is assuredly a flat joint of polytetrafluoroethylene or the like. The lid can be made of one or two pieces assembled by means of screws, the tightness between the two pieces being assured by a flat polytetrafluoroethylene joint. The means assuring the displacement of the sliding element can include a transmission shaft driven, for example by a pneumatic or hydraulic system. The evacuation passageway of the sliding element is linked by a flexible conduit and by means of valves with a products detector and then with reservoir collectors of fractions and eluants. The distribution chamber of the lid is linked by means of passageways to the distribution cell and the latter with the reservoirs of eluants and the solution to be chromatographed and with the surrounding air. A valve apparatus permits the desired selection of flow. The reservoirs of the solution to be divided and of the eluants are linked to a pneumatic circuit assuring the pressure necessary for accelerated discharge of liquids in the distribution chamber and for the passage of liquids through the support and the porous plates. It is preferable in the pneumatic circuit to use an inert gas such as nitrogen or argon.

The chromatographic column comprises a tube, for example of glass or stainless steel, according to the pressure to be applied and the diameter chosen. The diameter of the tube can vary in large proportions, it can be on the order of 10 to 250 mm in certain installations; it can be much greater in the case of industrial installations. The length of the tube varies according to its diameter, as for example, in a tube whose diameter is 80 mm, its length is preferably about 1000mm. Nevertheless in the case of more important preparative chromatography installations, it can go as far as 3500 mm or more, always in terms of thd diameter of the column. According to the preferred performance of the apparatus, the tube constituting the chromatographic column is vertically placed, its lower end being fixed to a support by means of screws.

The attached drawings show an illustrative form of the apparatus and a diagrammatic illustration of a system in which it is installed.

Figure 1:
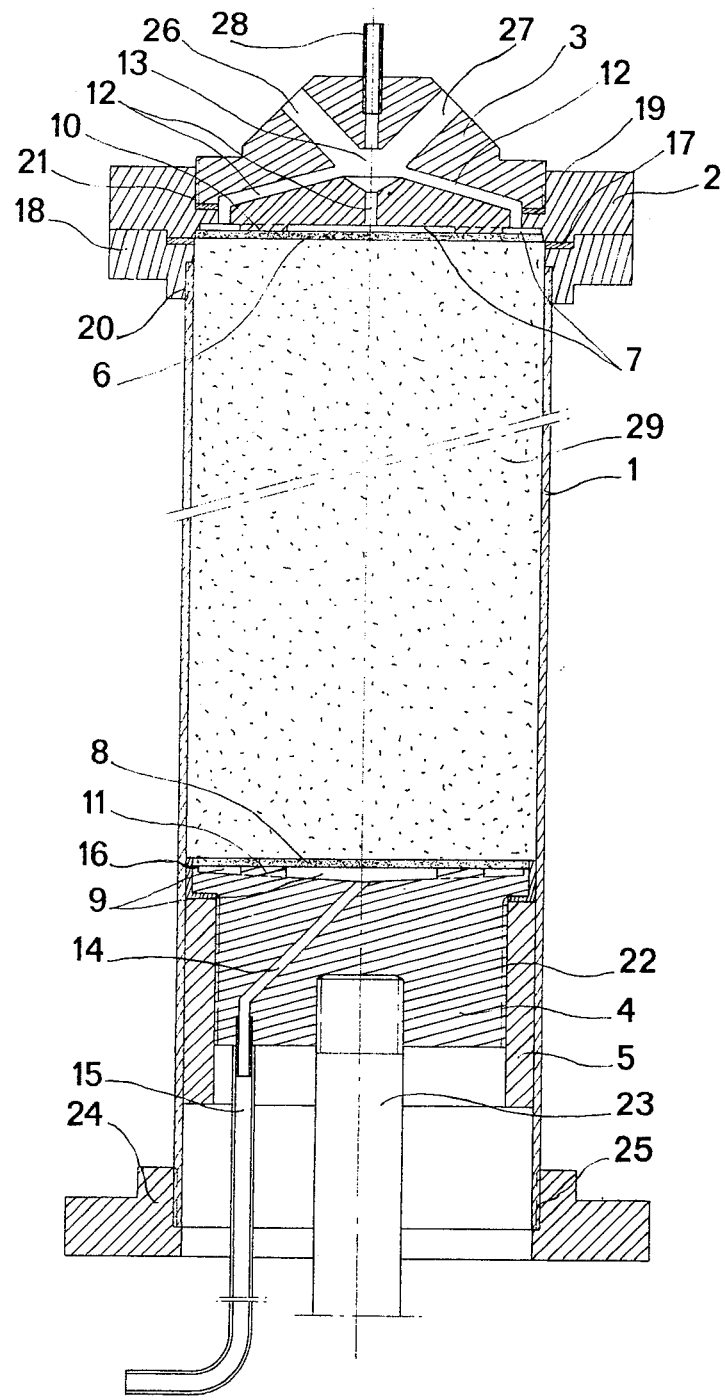
FIG. 1 is a vertical sectional view of the apparatus of the invention.
Figure 2:
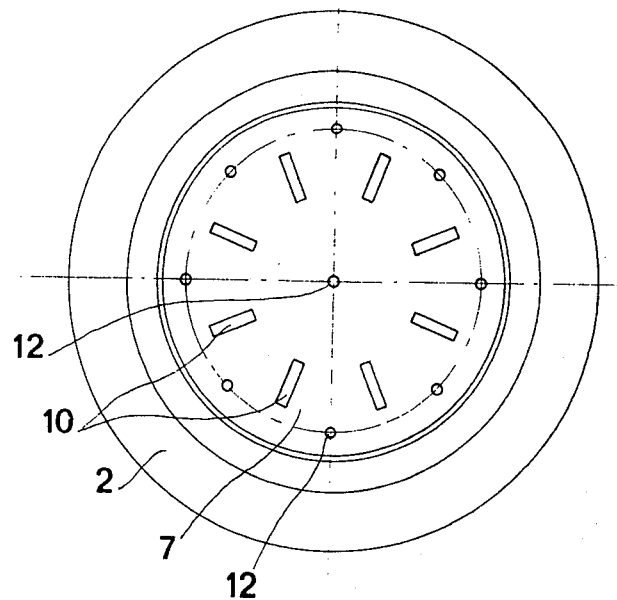
FIG. 2 is a bottom view of the column lid shown in FIG. 1 with the porous plate removed.
Figure 3:
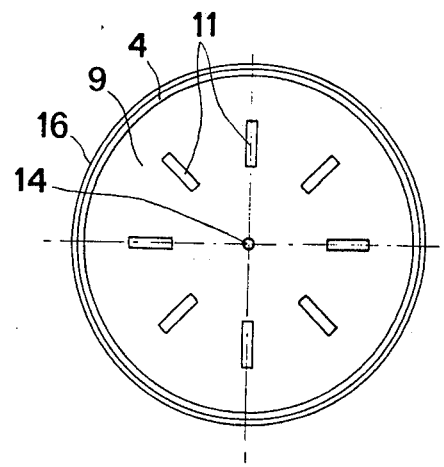
FIG. 3 is a top view of the sliding element shown in FIG. 1 with the porous plate removed.
Figure 4:
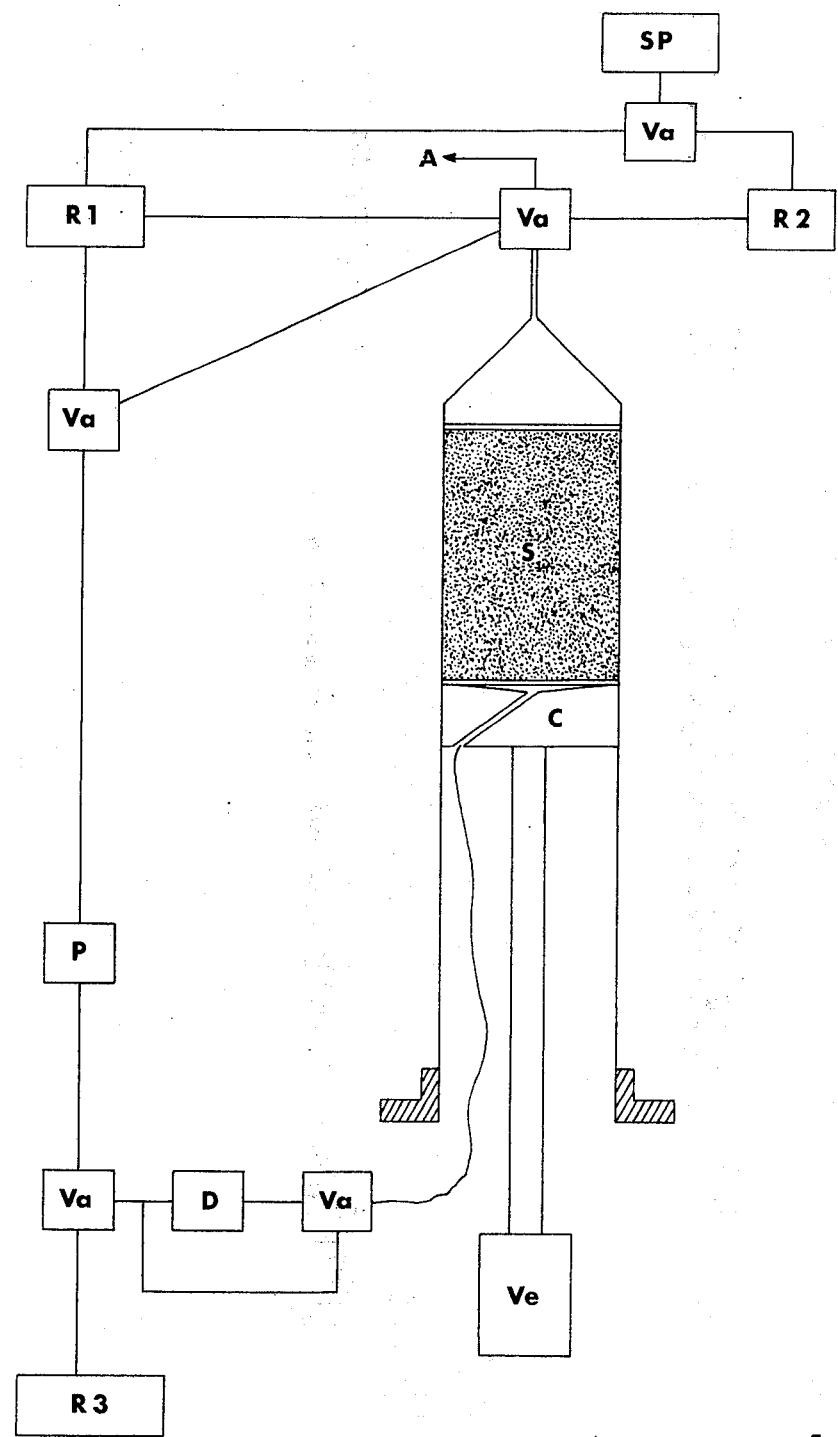
FIG. 4 is a schematic view of a chromatographic installation, of which the apparatus of the invention is a part.

Referring now to FIG. 1 of the drawings, a vertically disposed tube 1 represents a chromatographic column closed at the top by a removable lid comprising parts 2 and 3 and at the bottom by a sliding element in the nature of a piston 4 provided with an annular element 5. A porous plate 6 covers a distribution chamber 7 in the lid parts 2 and 3. Likewise, a porous plate 8 covers an evacuation cavity or sink 9 formed in the top of the piston 4. Radially placed bars 10 extend from part 3 of the lid into the distribution chamber 7. Radially placed bars 11 formed in the top of piston 4 extend into the sink 9. Passageways 12 link the distribution chamber 7 of the lid to a distribution cell 13 formed in part 3 of the lid. An evacuation passageway 14 links the evacuation cavity or sink 9 at the top of the piston 4 to a flexible conduit 15 which extends to the exterior of the apparatus. A lip joint 16 at the top of the piston 4 held by annular element 5 provides a sliding seal at the bottom of the device. A flat joint 17 between lid part 2 and flange 18 ensures a tight seal between these parts. Likewise, a flat joint 19 assures tightness between the parts 2 and 3 constituting the lid. The flange 18 is mounted on tube 1 be means of a threaded connection 20. The two parts of the lid 2 and 3 are assembled by means of a threaded connection 21. Piston 4 and annular element 5 of the sliding element are assembled by means of a threaded connection 22. A pressure transmission shaft 23 is secured to piston 4. The tube 1 is attached to a support 24 by means of threaded connection 25. An inlet passageway 26 in lid part 2 leads to the distribution cell 13 and an outlet passageway 27 allows the clearing of the distribution cell 13. A conduit 28 provides for the linkage of the apparatus with the exterior. A suspension of particles of an adsorbent material susceptible to giving the chromatographic separation is shown at 29. Referring now to FIG. 4, S represents the compressed bed of adsorbent material, $R_1$ is an eluant reservoir, $R_2$ is a reservoir for solutions to be chromatographed, $R_3$ is a reservoir for eluats, eluants and liquids to be recouped, D is a products detector, Va represents selector valves, Ve is a pneumatic or hydraulic jack for driving sliding element C, P is a pump for recirculation of liquids, and Sp is a source of pressurized gas.

In the operation of the apparatus the conduit 28 (FIG. 1) is appropriately linked by valves VA with the reservoir $R_2$ of solution to be fractionated, with one or several eluant reservoirs $R_1$, with the reservoir $R_3$ recouping the suspension liquid, and with the line A communicating with the surrounding air. In similar manner, the flexible conduit 15 which linked to products detector D then to the reservoirs $R_3$ of eluats and liquids to be recouped. Passageways 26 and 27 are closed.

As shown in FIG. 1, the piston 4 is in the first or retracted position, that is, in the lower position of its course. The two part connected lid 2 and 3 is raised and the particles suspension 29 of the adsorbent material capable of use for chromatographic adsorption, such as silica gel, is poured into the tube 1. Then the lid is replaced and fixed to the tight flange 18 by means of screws or the like. With the help of valves VA, the distribution chamber 7 is then linked, by means of the distribution cell 13 and the conduit 28 with the reservoir of solution to be chromatographed, on the one hand, and on the other, the evacuation cavity 9 is linked by means of the passageway 14 and the flexible conduit 15 with a reservoir $R_3$ intended to receive the liquid expressed from the suspension 29. Lid passageway 27 can be linked to reservoir $R_3$.

The operation of the pneumatic or hydraulic jack Ve, for example, displaces, by means of the transmission shaft 23 the sliding element comprising piston 4 and assembled parts towards the lid. The sliding element thus exerts a pressure on the suspension 29 contained in the tube 1 and discharges the suspension liquid through the porous plates 6 and 8 into reservoir $R_3$.

One can attain, in a representative example of execution, the compression stage of the chosen bed material and the desired compression of particles when the sliding element has gone approximately two-fifths of the height of the column. Once the bed compression has been produced, the pressure of the sliding element is maintained for the duration of the actual chromatography, that is, during the introduction of the matter to be fractionated as well as during the elution of the materials adsorbed on the particles of the bed.

It will be understood that the displacement of the sliding element and consequently the degree of compression of the bed, as well as the pressure of said element during the chromatographic operations are selected according to the quantity, the density of the suspension, the granulometry and the nature of the particles of the adsorbent material, as well as the nature of the solution to be chromatographed and the eluants. It is also necessary to take into account the pressure of the fluids intervening during the chromatographic operations.

In the illustrative case, particles of silica gel were chosen having a diameter of 5 to 40 $\mu$ and a suspension was made from 1000 g. of silica gel and 2500 $cm^3$ of eluant. The pressure exerted by the jack and by means of the sliding element can be on the order of 2 to 20 $kg/cm^2$, preferably from 5 to 10 $kg/cm^2$.

Due to the judicious selection of the parameters as: the porosity of the plates, the granulometry and the nature of the support particles as well as the pressure exerted on the sliding element, the operation of compression of the particulate material can be executed in the space of about 5 or 6 minutes. This time lapse, compared to the lapse necessary for the method of traditional preparation of the adsorbent bed for chromatography, calculated by the hours necessary for the sedimentation of the adsorbant material particles, emphasizes the advantages of the time gain realized as a result of the apparatus of this invention.

Once the suspension is submitted to pressure and the bed of adsorbent material compressed, the actual chromatography begins by appropriate operation of the valves Va. The reservoir containing the solution of material to be separated is placed in communication with the conduit 28 and with the distribution chamber 7 through the distribution cell 13. The reservoir containing the solution of materials to be separated can communicate with a pnuematic system, for example, based on argon or nitrogen. The gas is introduced under pressure in said reservoir $R_2$ and thus the passages of the solutions is facilitated to the distribution chamber 7, then through the porous plate 6, through the compressed bed S and finally through the porous plate 8 to the evacuation cavity 9 when the solvent is regained by passage through the evacuation passageway 14 and the conduit 15 to a suitable reservoir.

During the passage of the solution across the compressed bed, the selective adsorption of the materials to be separated occurs on the adsorbent particles in the form of different ring divisions.

The next step is the elution of materials to be separated by placing the column in communication with one or more eluant reservoirs $R_1$. The elution is also facilitated by means of the pneumatic system Sp, based on argon or nitrogen. This operation is carried out in a similar manner to that described previously for the solution of materials to be separated.

The eluants, after their passage through the porous plate 8 are sent through the flexible conduit 15 to the products detector D in order to identify them, then to the respective reservoirs of eluants $R_3$ where the products sought are isolated.

The products detector D can be, for example, a spectrophotometer, a polarimeter or a refractometer. However, instead of proceeding to the elution of materials adsorbed on the bed as described above, the apparatus of the invention can be used to advantage in a different manner.

With the apparatus, the successive elution of different rings of fractions to be separated may avoided. Once the materials to be fractionated are adsorbed on the bed in the form of rings and the volume of retained solvent has left the column, the column lid is lifted and the sliding element is raised again with the help of the jack. In raising the sliding element the compressed bed containing the adsorbed materials to be fractioned is expelled in the form of a solid body.

This bed is analyzed either by ultraviolet rays or by projection on a straight longitudinal band of a specific indicator, in order to determine the respective positions of the different fraction rings to be separated. The bed is then cut into sections according to the rings and the rings are treated separately with appropriate solvents and the fractioned products are thus isolated with no difficulty.

In the case where one proceeds to elution of the products adsorbed on the bed by a series of elution operations, the said bed having once been used, can, after supplementary rinses, eventually be used again for new chromatography without losing its essential qualities.

The advantage that the use of the apparatus represents in a chromatographic installation is evident. The time gain realized due to the accelerated compression of the particles into a bed by means of the apparatus, while respecting the bed qualities already emphasized, permits an important reduction in the time necessary for the execution of the whole chromatographic operation, while improving the resolution of the materials to be chromatographed. The possibility of using the apparatus in combination with a pneumatic system, based on argon or nitrogen is another advantage of the apparatus.

It is also important to note that at the time of utilization of the bed of chromatographic adsorbent obtained by application of the apparatus, an important reduction in the quantities of eluants necessary for fractionating the products is ascertained.

If for example, the apparatus is used for chromatography under pressure, the optional conditions can be selected in terms of two parameters; compression pressure of the bed and gas pressure by which the elution of the support is effected.

The quality factor pertaining to column chromatography is the capacity to produce the rings as narrow as possible, this is what is termed efficacity. This efficacity of a chromatographic column is determined by analogy to a rectification column, by the theoretical number of plates or stages.

At the time of trials conducted with the apparatus of this invention, integrated with a chromatographic pressure installation, it was ascertained that for a tube 80 mm in diameter and 1000 mm in length, filled with 1 kg. of silica gel particles of 10-40 $\mu$ diameter obtained by compression pressure on the order of 6kg/cm$^2$, the maximum efficacity of the column is about 7000 stages per meter and for the quantity of injected solution (10 mg dissolved in 10 cm$^3$ of solvent). By comparison, for the conventional column of the same dimensions, the maximum efficacity is 2000 stages per meter.

It goes without saying that the invention is not limited to the illustrative embodiments described and presented. It encompasses all variations of the invention resulting from the same established principle.

What is claimed is:

1. Chromatographic apparatus adapted to contain a bed of particulate adsorbent material in column form, said apparatus comprising a tube; a lid removably mounted at one end of the tube, said lid being permeable to liquids and gases while retaining particulate adsorbent material; a slidable element movably mounted within said tube so as to provide a chamber of variable volume for particulate adsorbent material between said lid and said slidable element, said slidable element being permeable to gases and liquids while retaining particulate adsorbent material and movable the length of the tube; and means for communicating a force to said slidable element to displace said slidable element along the axis of the tube, said force being sufficient to compress particulate adsorbent material contained in said tube into the consistency of a solid body and said means being effective to maintain said particulate adsorbent material under compression and being capable of providing sufficient force to extrude all the solid body of adsorbent material from the end of the tube when the lid is removed.

2. Apparatus according to claim 1 wherein the removable lid permeable to liquid and gases comprises a member having a porous plate at its base.

3. Apparatus according to claim 1 wherein the means of communicating a force to the slidable element is a pneumatic or hydraulic jack.

4. Apparatus according to claim 1 wherein the slidable element is in the form of a piston having at its head a porous plate permeable to liquids and gases.

5. Apparatus according to claim 2 wherein the lid member is provided with a fluid distribution chamber adjacent said porous plate and wherein said fluid distribution chamber communicates by means of a plurality of passageways to a distribution cell which in turn communicates to the exterior of the tube.

6. Apparatus according to claim 4, wherein the slidable element in piston form is provided with an evacuation cavity under the porous plate in the head of said piston and wherein said evacuation cavity is provided with an evacuation passageway leading to an outlet conduit.

7. Apparatus according to claim 5, wherein the distribution chamber is provided with radially placed bars of a height equal to the depth of the chamber and wherein said chamber is linked to the distribution cell by a central passageway and radially placed passageways converging on said cell.

8. Apparatus according to claim 6, wherein the evacuation cavity is in sink form having radially placed bars of a height corresponding to the profile of the sink and converging on a central evacuation passageway.

9. The chromatographic apparatus of claim 1 wherein the tube has a diameter of from 10 to 250 mm.

* * * * *